(12) United States Patent
Lai et al.

(10) Patent No.: US 6,287,845 B1
(45) Date of Patent: Sep. 11, 2001

(54) **STRAINS OF *STREPTOMYCES* AND RELEVANT USES THEREOF**

(75) Inventors: Li-Hsiu Lai; Mann-Yan Kuo; Ming Shiang, all of Taipei (TW)

(73) Assignee: Development Center for Biotechnology, Taipei (TW)

(*) Notice: Subject to any disclaimer, the term of this patent is extended or adjusted under 35 U.S.C. 154(b) by 0 days.

(21) Appl. No.: 09/841,977

(22) Filed: Apr. 25, 2001

Related U.S. Application Data

(62) Division of application No. 09/571,700, filed on May 15, 2000.

(51) Int. Cl.⁷ ............................. C12N 1/20; C12P 1/00
(52) U.S. Cl. ............................ 435/253.5; 435/41
(58) Field of Search ................. 435/253.5, 243, 435/78, 41, 170; 424/405

(56) References Cited

U.S. PATENT DOCUMENTS

| | | | | |
|---|---|---|---|---|
| 3,067,099 | * | 12/1962 | McCormick et al. ............... | 167/65 |
| 3,067,100 | * | 12/1962 | Hata et al. ....................... | 167/65 |
| 3,927,210 | * | 12/1975 | Stapley et al. ................... | 424/118 |
| 3,992,524 | * | 11/1976 | Umezawa et al. ................ | 424/115 |
| 4,383,037 | * | 5/1983 | Fujiwara et al. .................. | 435/78 |
| 5,239,064 | * | 8/1993 | Hoehn et al. ..................... | 536/6.5 |

OTHER PUBLICATIONS

ATTC: Catalogue of Bacteria & Bacteriophages, 18th ed. pp. 26, 1992.*

* cited by examiner

Primary Examiner—Christopher R. Tate
Assistant Examiner—Patricia Patten
(74) Attorney, Agent, or Firm—Morgan & Finnegan, LLP

(57) ABSTRACT

The invention relates to isolates of *Streptomyces orientalis* Y31014 and *Streptomyces melanogenes* Y31042-1 can be effectively control whiteflies.

The invention also concerns a novel biopesticide and its use to control pests.

4 Claims, No Drawings

STRAINS OF *STREPTOMYCES* AND RELEVANT USES THEREOF

This is divisional of co-pending application Ser. No. 09/571,700, filed May 15, 2000.

FIELD OF THE INVENTION

The invention relates to novel strains of *Streptomyces orientalis* and *Streptomyces melanogenes;* and the use of the strains.

BACKGROUND OF THE INVENTION

There are a variety of insects that cause major economic losses in agriculture and spread diseases among plants. Whitefly is one of the most notorious agricultural pests in the world. For example, in 1981, the sweet potato whitefly, *Bemisia tabaci* (Gennadius), caused 100 million US dollar damage in cotton, cucurbits, and lettuce in the United States. In 1986, whitefly became a problem in Florida where *B. tabaci* caused approximately US$2 million of damage to Florida's US$8 to 10 million poinsettia crop.

Whitefly is now known to feed on more than 500 different plants. For example, sweet potato, tomato, beans, cotton, carrot, cassava, squash, lettuce, pepper, egg plant, watermelon, and cucumber are all known hosts to the pest. It is also known that sweet potato whitefly may transmit more than 70 diseases caused by virus and microorganisms.

Silverleaf whitefly (*B. argentifolii* Bellows and Perring) was first found in Taiwan in 1991. In 1995, silverleaf whitefly was responsible for 1000 hectares of agriculture losses in Taiwan.

Whitefly is very difficult to control with conventional pesticide application. Many factors contribute to the lack of control obtained with pesticides. Only few commercially available pesticides are effective against whiteflies. However, these pesticides are only effective if care is taken in a very thorough application several times a week. In addition, whiteflies spend most of their life on the undersides of leaves; therefore, growers must adjust their management practices to permit increased pesticide coverage there. The spacing of the plants must be such that the chemical spray can penetrate the canopy and reach all surfaces of the plants.

Further, the ineffective use of the chemical pesticides may be costly, and has other significant drawbacks, such as the pollution to the environment, and the potential health hazards to agricultural workers and to consumers.

Therefore, safer and more effective methods for controlling whiteflies are needed. Although biological control agents have been studied for years, to date no biological control agent has been commercially successful for the control of whiteflies.

U.S. Pat. Nos. 4,942,030 and 5,413,784 disclosed the utilization of fungi *Paecilomyces fumosoroseus* and *Beauveria bassiana* in controlling sweet potato whitefly.

Streptomyces sps. have been widely used in the production of antibiotic materials. However, thus far, no Streptomyces sp. had been identified as having biopesticidal activity against whiteflies.

SUMMARY OF THE INVENTION

New strains in the Streptomyces genus, designated *Streptomyces orientalis* Y31014 and *Streptomyces melanogenes* Y31042-1, surprisingly have been found. The strains are found to be active against whiteflies.

Therefore, in the first aspect of the invention, the novel strains *Streptomyces orientalis* Y31014 and *Streptomyces melanogenes* Y31042-1 are provided.

In the second aspect of the invention, a biopesticide composition comprising the novel strains is provided.

In a further aspect of the invention, the method for controlling pests by contacting pests with the novel strains is provided.

IDENTIFICATION AND CHARACTERIZATION OF THE MICROORGANISMS

The novel Y31014 and Y31042-1 strains were isolated from a soil sample taken form Miaoli, Taiwan, ROC. These microorganisms have been identified by the Food Industry Research and Development Institute, Shin-Chu, Taiwan, ROC as strains of *Streptomyses orientalis* and *Streptomyces melanogenes,* respectively. The methods and results are as follows:

Taxonomic and morphologic characterization was made using the methods recommended by the International Streptomyces Project (ISP) for characterizing Streptomyces species.

1. Cell Wall Analysis

Dried cells (10 mg) were put into a test tube containing 1 ml of 6N HCl, and were hydrolyzed in 100° C. for 18 hours. Hydrolysate was filtered and dried. The dry powder was dissolved in 0.4 ml of distilled water, and poured on a PTLC plate. Methanol-$H_2O$—6N HCl-pyridine was used as the developing solution. Ninhydrin was then applied after an air-drying process. Diaminopimelic acid (DAP) produces a yellowish green color, while other amino acids produce a purple red color. See Komagata, et al.,"Lipid and Cell-Wall Analysis in Bacterial Systematics," Meth. Microbiol. 19:161–207 (1987).

2. Whole Cell Sugar Analysis

Dried cells (50 mg) were put into a test tube containing 1 ml of 1N $H_2SO_4$, and were hydrolyzed in 100° C. for 2 hours. The pH of the hydrolysate was adjusted to the range of 5.0–5.5 by saturated $Ba(OH)_2$. The hydrolysate was then centrifuged. The upper suspension was collected and concentrated. The concentrate was dissolved in 0.4 ml of distilled water and then poured on a filter. N-butanol-$H_2O$-pyridine-toluene was uses as developing solution. Aniline phthalate was applied to develop the color of the sugars. Six-carbon sugars will result in a brown color, and five-carbon sugars will result in pink color after an air-drying process. See Komagata, et al.,"Lipid and Cell-Wall Analysis in Bacterial Systematics," Meth. Microbiol. 19:161–207 (1987).

3. Cultural Characteristics Analysis

Cells were cultured on yeast extract-malt extract agar (ISP# 2 medium), oatmeal agar (ISP# 3 medium), inorganic salts starch agar (ISP# 4 medium), and glycerol-asparagine agar (ISP# 5 medium), respectively for 14 days to observe the vegetative mass, aerial mass, spore production and pigment production. See Shiring et al., "Methods for Characterization of Streptomyce species," Int. J. Syst. Bacteriol., 16:313–340 (1966).

4. Melanoid Pigment Production Analysis

Cells were cultured on tryptone-yeast extract broth (ISP# 1 medium), peptone-yeast extract iron agar (ISP# 6 medium) and tyrosine agar (ISP# 7 medium) for 7 and 14 days respectively, to observe the melanoid pigment production. See Shiring et al., "Methods for Characterization of Streptomyce species," Int. J. Syst. Bacteriol., 16:313–340 (1966).

5. Morphological Characteristics

Cells together with agar were cut from ISP# 2, 3, 4, and 5 media, dehydrated in oven, and coated with gold in an ion-coater. The morphology was studied using a scanning electron microscope (SEM).

6. Sugar Utilization and Physical Characteristics Analysis

Cells were cultured on ISP# 9 medium containing 1% sugar (D-glucose, L-arabinose, D-xylose, sucrose, D-fructose, raffinose, rhamnose, I-inositol, D-mannitol, cellulose, salicin) for 7 and 14 days to observe cell growth. See Shiring et al., "Methods for Characterization of Streptomyce species," Int. J. Syst. Bacteriol., 16:313–340 (1966).

The results are shown in Tables 1 to 4.

TABLE 1

Cultural characteristics of Y31014

| Medium | Growth | Substrate mycelium | Aerial mycelium | Sporulation | Soluble pigment |
|---|---|---|---|---|---|
| Yeast extract-malt extract agar (ISP #2 medium) | Well | Deep orange yellow | Yellowish white | Good | None |
| Oat meal agar (ISP # 3 medium) | Well | Brilliant yellow | Yellowish white | Moderate | None |
| Inorganic salt agar (ISP #4 medium) | Well | Strong yellow | Yellowish white | Good | None |
| Glycerol asparagine agar (ISP #5 medium) | Moderate | Brilliant yellow | Pale yellow | Poor | None |

TABLE 2

Physiological characteristics of Y31014

| Cabon source | Y31014 |
|---|---|
| D-glucose | +* |
| D-xylose | + |
| D-fructose | + |
| Sucrose | – |

TABLE 2-continued

Physiological characteristics of Y31014

| Cabon source | Y31014 |
|---|---|
| L-arabinose | + |
| Rhamnose | – |
| Raffinose | + |
| D-mannitol | + |
| I-inositol | + |
| Cellulose | – |
| Salicin | + |

*+: positive reaction, –: negative reaction

TABLE 3

Cultural characteristics of Y31042-1

| Medium | Growth | Substrate mycelium | Aerial mycelium | Sporulation | Soluble pigment |
|---|---|---|---|---|---|
| Yeast extract-malt extract agar (ISP #2 medium) | Moderate | Strong brown | Light gray | Moderate | None |
| Oat meal agar (ISP # 3 medium) | Moderate | Strong yellowish pink | Grayish yellowish pink | Poor | None |
| Inorganic salts starch agar (ISP #4 medium) | Moderate | Deep orange | Light gray | Poor | None |
| Glycerol asparagine agar (ISP #5 medium) | Poor | Yellowish white | Light pale pink | Poor | None |

TABLE 4

Physiological characteristics of Y31042-1

| Cabon source | Y31042-1 |
| --- | --- |
| D-glucose | + |
| D-xylose | + |
| D-fructose | + |
| Sucrose | − |
| L-arabinose | + |
| Rhamnose | − |
| Raffinose | + |
| D-mannitol | + |
| I-inositol | + |
| Cellulose | − |
| Salicin | − |

*+: positive reaction, −: negative reaction

Cell Wall Amino Acid and Whole Cell Sugar Analyses

The cell wall amino acid and whole cell sugar contents of both strains Y31014 and Y31042-1 are LL-DAP, and glucose, ribose, respectively. These strains belong to chemotype IC according to the classification by Lechevalier et al., "The Chemotaxonomy of Actinomycetes," In: Dietz, A. and D. W. Thayer (eds.) Actinomycete Taxonomy. SIM Special Publication NO. 6. USA, and are assigned to the genus Streptomyces.

Species Identification

The comparison with standard isolate of strains (Actinobase and International Journal of systematic Bacteriology) reveals that Y31014 is most related to *S. orientalis*, and, and Y3 1042-1 is mostly to *S. melanogenes*.

Deposition Information

The cultures of *Streptomyces orientalis* Y31014 and *Streptomyces melanogenes* Y31042-1 have been deposited with the American Type Culture Collection, (ATCC, 10801 University Boulevard, Manassas, Va. 20110-2209, USA) on Aug. 20, 1999 in accordance with the Budapesst Treaty, and assigned the accession No. ATCC PTA-558 and PTA-557 respectively.

DETAILED DESCRIPTION OF THE INVENTION

The invention provides biological pure cultures of *Streptomyces orientalis* Y31014 and *Streptomyces melanogenes* Y31042-1.

It is known in the art to obtain mutants of microorganisms without altering the characteristic thereof. For instance, mutants may be obtained by treatment with physical or chemical mutagens, such as UV light, X-rays, gamma-rays and chemical such as n-methyl-N'-nitro-N-nitrosoguanidine. It is also known in the art to obtain natural variants by e.g. screening cultures of the parent strain. Therefore, the invention also pertains to the mutants or variants of *Streptomyces orientalis* Y31014 and *Streptomyces melanogenes* Y3 1042-1 which retain the characteristics of the strains.

The novel isolates *Streptomyces orientalis* Y31014 and *Streptomyces melanogenes* Y31042-1 are the first known Streptomyces which is highly virulent to whiteflies.

*Streptomyces orientalis* Y31014 and *Streptomyces melanogenes* Y31042-1 can attach to and subsequently penetrate the cuticle of an insect host. After penetrating the target pest's cuticle, the mycelium begins to enter the host tissues and the dying insect is filled with mycelium. Spores are produced on the external surface of the host. These spores are dispersed and capable of infecting new host insect pests.

*Streptomyces orientalis* Y31014 and *Streptomyces melanogenes* Y31042-1 work rapidly, with a remarkable 100 percent kill of pupal stage silverleaf whitefly within 3 to 7 days of application. Up to 70 percent of the pest can be killed at the dilution rate of $10^{-3}$ of the cultural broth. The concentrations from about $7 \times 10^9$ to $7 \times 10^6$ CFU per milliliter of carrier can be used.

In accordance with the purpose for application, the fermented cultural broth can be used directly or formulated as compositions suitable for spraying, atomizing, dusting, spreading or pouring. For instance, the compositions can be formulated as ready-to-spray solutions, wettable-powders, suspensions, highly concentrated aqueous, oily, or other suspensions or dispersions, emulsions, oil dispersions, pastes, dusts, or granules. As with the application, the culture broth and the composition of the invention may be applied directly to the insect, the foliage of the plants, or the surroundings.

To prepare the biopesticide composition, the pure culture of the microorganism may be removed from the moisture content of the growth medium. The compositions may be prepared in a known manner, e.g. by extending the active ingredient with agriculturally acceptable carriers, auxiliaries or dilutents, such as emulsifiers, and dispersants, or surfactants, which does not inhibit the growth of the microorganism.

Carriers suitable for use in the invention include, but not limited to, ground natural or synthetic minerals, e.g. calcite, talc, diatomite, montmorillonite, attapulgite, and the like. To improve the physical properties of the compositions, highly dispersed silicates or highly dispersed absorptive polymers may be added.

Emulsifiers suitable for use in the invention include, but not limited to, nonionic and anionic emulsifiers, e.g. polyoxyethylene fatty alcohol ethers, alkylsulfonates, arylsulfonates, and the like.

Dispersants suitable for use in the invention include, but not limited to, lignosulfite waste liquors and methylcellulose, and the like.

Suitable surfactants include, but not limited to, the conventional surfactants disclosed in Mc Cutcheon's Detergents and Emulsifiers Annual, MC Publishing Corp., Glen Rock, N.J., 1988; and Encyclopedia of Surfactants, vol. I–III, Chemical Publishing Co., New York, 1980–1981.

The biopesticide composition of the invention is specific to Bemisia, and therefore can be used to treat and prevent the diseases caused by the group, e.g. aphides, leafhoppers, and whiteflies.

The fermented cultural broth of the present invention may also be applied in conjunction with a powder or granular carrier. As with spray application, the powder or granular formulation may be applied directly to the insect, the foliage of the plants, or the surroundings. To prepare the pure culture of the microorganism for mixing with the powder or granular carrier, it may be removed from the moisture content of the growth medium and combined with any other granular or powder material which does not inhibit the growth of the microorganism. Although the microorganism may be applied in conjunction with a granular carrier, application may be easier and more uniform if the carrier and the fermented cultural broth has a consistency. The biopesticide composition of the invention results in the application of a mixture which comprises the spores of the microorganism and mycelia together with a carrier. The presence of both the spores and the mycelia facilitates colonization of the target insects.

EXAMPLE 1

The Selection of the Strains Y31014 and Y31042-1

The stored microorganisms were first transferred on PDA plates and incubated at 30° C. for 7 days. One tenth of microorganism was taken from PDA plate, and inoculated to a 500 ml round bottle flask containing 100 ml NGY medium (NB 8 g, glucose 10 g, yeast extract 5 g, water 1l). The microorganism was cultivated at 30° C., 200 rpm for 24 hours. 5 ml of the culture were transferred to another 500 ml round bottle flask containing 100 ml of SSM 331 (corn starch 30 g, Supro 620 30 g, molasses 10 g, water 1l) medium and cultured for 72 hours. The culture was diluted and ready for the activity selection tests.

Two lines of silverleaf whiteflies in pupal stage were put on a stage glass, on which each line contains 5 bugs in a distance of 1 cm. 3 μl of the each diluted culture prepared as above was dropped on each bug. The stage glass was put into a 9 cm petri dish with a filter membrane containing 1 ml of water. The results were observed after 3 to 7 days with microscope.

It is found that the death rate on the first 3 days was not high. 7 days later, at the dilution rate of $10^{-2}$, the death rates of the bugs which are treated with the strains Y31014 and Y31042-1 were 100%. White colonies were found on the bodies of the dead whiteflies infected by the strain Y31014. The bodies infected by the strain Y31042-1, only few colonies were observed, but whole bug turned into red-brown color.

EXAMPLE 2

The Activity Studies of the Strains Y31014 and Y31042-1

To determine whether the effective material(s) caused the death of the whitefly is the antibiotic material(s) produced by the strains Y31014 and Y31042-1, or by the microorganisms per se, the following studies were proceeded.

The cultures of the strains Y31014 and Y31042-1 were centrifuged at 15000 rpm for 15 min., the supernatants and the pellets were collected separately for further tests. In addition, the sterilized cultures of the strains Y31014 and Y31042-1, or the extracts of the cultures by acetone or acetyl acetate were also prepared. These samples were applied to the whitefly as the process illustrated in Example 2. The results are shown in Tables 5 and 6.

TABLE 5

| | Death Rate (%) | | | |
| --- | --- | --- | --- | --- |
| Strain Y31014 | *250X | 500X | 750X | 1000X |
| Cultural Broth | 90 | 60 | 50 | 50 |
| Supernatant | 50 | 60 | 50 | 50 |

TABLE 5-continued

| | Death Rate (%) | | | |
| --- | --- | --- | --- | --- |
| Strain Y31014 | *250X | 500X | 750X | 1000X |
| Pellet | 90 | 70 | 70 | 70 |
| Sterilized Culture | 0 | 0 | 0 | 0 |
| Acetone Extract | 0 | 0 | 0 | 0 |
| Acetyl Acetate Extract | 0 | 0 | 0 | 0 |

*dilution rate

TABLE 6

| | Death Rate (%) | | |
| --- | --- | --- | --- |
| Strain Y31042-1 | *100X | 250X | 500X |
| Cultural Broth | 60 | 50 | 40 |
| Supernatant | 0 | 0 | 0 |
| Pellet | 70 | 70 | 10 |
| Sterilized Culture | 0 | 0 | 0 |
| Acetone Extract | 0 | 0 | 0 |
| Acetyl Acetate Extract | 0 | 0 | 0 |

*dilution rate

As illustrated in Table 6, the biological activity of the strain Y3 1042-1 only showed in the cultural broth and the pellet. According to Table 5, the biological activity existed in the supernatant of the strain Y31014, however, the activity was lower and white colonies were found on the dead bodies. It is suggested that the effectual material of the cultures of the strains Y31014 and Y31042-1 is the microorganisms per se. The biological activity of the supernatant of the strain Y31014 is mostly originated from the spores which cannot be fully separated by centrifugation.

What is claimed is:

1. A biologically pure culture of the micoorganism *Streptomyces melanogenes* Y31042, or a mutant or variant thereof having the characteristics:
   a) a yellowish pink to brown substrate mycelium with a grayish aerial mycelium with moderate growth in a culture medium selected from the group consisting of yeast extract-malt extract agar, oat meal agar, or inorganic salt agar;
   b) grown in a culture medium containing a sugar selected from the group consisting of D-glucose, D-xylose, D-fructose, L-arabinose, raffinose, D-mannitol, and I-inositol; and
   c) being highly virulent to white flies at a dilution of 1:100 to 1:1000 of a culture broth of the microorganism to water.

2. The microorganism of claim 1, which is under the accession No. ATCC PTA-557.

3. A biopesticide composition comprising an effective amount of at least one biologically pure culture according to any one of claims 1 to 2 and an agriculturally acceptable carrier.

4. A method for controlling a targeted pest comprising applying an effective amount of at least one biologically pure culture according to any one of claims 1 to 2.

* * * * *